United States Patent
Sharma

(10) Patent No.: US 7,738,961 B2
(45) Date of Patent: Jun. 15, 2010

(54) METHOD AND APPARATUS FOR TREATMENT OF THE GASTROINTESTINAL TRACT

(75) Inventor: Virender K Sharma, Paradise Valley, AZ (US)

(73) Assignee: Endostim, Inc., St. Louis, MO (US)

( * ) Notice: Subject to any disclaimer, the term of this patent is extended or adjusted under 35 U.S.C. 154(b) by 253 days.

(21) Appl. No.: 11/539,645

(22) Filed: Oct. 9, 2006

(65) Prior Publication Data
US 2008/0086179 A1    Apr. 10, 2008

(51) Int. Cl.
*A61N 1/36* (2006.01)
(52) U.S. Cl. ......................................................... 607/40
(58) Field of Classification Search .................... 607/40
See application file for complete search history.

(56) References Cited

U.S. PATENT DOCUMENTS

| | | | |
|---|---|---|---|
| 5,423,872 A | 6/1995 | Cigaina | |
| 6,216,039 B1 | 4/2001 | Bourgeois | |
| 6,587,719 B1 | 7/2003 | Barrett | |
| 6,591,137 B1 * | 7/2003 | Fischell et al. | 607/40 |
| 6,611,715 B1 | 8/2003 | Boveja | |
| 6,615,084 B1 | 9/2003 | Cigaina | |
| 6,760,626 B1 | 7/2004 | Boveja | |
| 6,879,859 B1 | 4/2005 | Boveja | |
| 6,901,295 B2 | 5/2005 | Sharma | |
| 2003/0144708 A1 | 7/2003 | Starkebaum | |
| 2004/0015201 A1 | 1/2004 | Greenstein | |
| 2004/0024428 A1 | 2/2004 | Barrett | |
| 2004/0039427 A1 | 2/2004 | Barrett | |
| 2004/0172088 A1 | 9/2004 | Knudson | |
| 2004/0193229 A1 * | 9/2004 | Starkebaum et al. | 607/40 |
| 2005/0049655 A1 | 3/2005 | Boveja | |
| 2005/0065571 A1 | 3/2005 | Imran | |
| 2005/0070974 A1 | 3/2005 | Knudson | |
| 2005/0075678 A1 | 4/2005 | Faul | |
| 2005/0090873 A1 | 4/2005 | Imran | |
| 2005/0131486 A1 | 6/2005 | Boveja | |
| 2005/0137643 A1 * | 6/2005 | Mintchev | 607/40 |
| 2005/0137644 A1 | 6/2005 | Boveja | |
| 2005/0143787 A1 | 6/2005 | Boveja | |
| 2005/0149141 A1 | 7/2005 | Starkebaum | |
| 2005/0149142 A1 | 7/2005 | Starkebaum | |
| 2005/0149146 A1 | 7/2005 | Boveja | |
| 2005/0222637 A1 | 10/2005 | Chen | |
| 2006/0036293 A1 * | 2/2006 | Whitehurst et al. | 607/40 |
| 2006/0167498 A1 * | 7/2006 | DiLorenzo | 607/2 |

\* cited by examiner

*Primary Examiner*—Scott M Getzow
*Assistant Examiner*—Michael Kahelin
(74) *Attorney, Agent, or Firm*—Patentmetrix

(57) ABSTRACT

A method and device for electrically stimulating one or more structures in the gastrointestinal tract as described. The one or more structures are preferably selected from the upper esophageal sphincter, the esophagus and gastric fundus. The method may involve the step of arranging a plurality of stimulating electrodes adjacent one or more structures which may further include the lower esophageal sphincter, the stomach, the pyloric sphincter, the small intestine, the colon and the vagus. The method and device may further include sensing electrodes to detect change in one or more physiological parameters in the gastrointestinal tract and modulate the stimulating electrodes in response to the change. The device comprises a pulse generator, a power source, a plurality of stimulating electrode set, one or more sensing electrodes and means for varying activity of the stimulating electrodes in response to change detected in the gastrointestinal tract. The method and device may be used to treat obesity and/or GERD.

14 Claims, 9 Drawing Sheets

Fig_2

METHOD AND APPARATUS FOR TREATMENT OF THE GASTROINTESTINAL TRACT

FIELD OF THE INVENTION

THIS INVENTION relates generally to a method and apparatus for electrical stimulation of a selected gastrointestinal muscle or muscles.

More particularly, the invention relates to a method and apparatus for electrical stimulation of one or more portions of the gastrointestinal tract to increase muscle tone and/or induce muscle spasm in the portion or to stimulate one or more nerves. The initiation or duration of the electrical stimulation may be modified by changes in physiological parameters which may be monitored by the invention. The invention may be particularly suited to decreasing caloric intake or decreasing the tendency to caloric intake, thereby providing a means of weight control.

BACKGROUND OF THE INVENTION

It is generally known that obesity is a common condition and a major public health problem in developed nations, including the United States of America. Today, 64.5% of American adults, about 127 million people, are either overweight or obese. Data demonstrated 300,000 Americans die prematurely from obesity related complications each year. More than 25% of children today are overweight or obese in the United States of America, hence the number of overweight Americans has increased steadily and will continue to increase in the coming years. Obesity costs the United States an estimated $100 billion annually in direct and indirect health care expenses and in lost productivity. This trend is also apparent in many other developed countries.

Morbid obesity is defined as more than 100 pounds greater than normal body weight or a body mass index (BMI), greater than 40 $kg/m^2$ and is present in 5% of the U.S. population. A BMI greater than 30 $kg/m^2$ is associated with significant co-morbidities. Morbid obesity is associated with many diseases and disorders, including diabetes, hypertension, heart attacks, strokes, dyslipidemia, sleep apnea, Pickwickian Syndrome, asthma, lower back and disc disease, weight-bearing osteo-arthritis of the hips, knees, ankles and feet, thrombophlebitis and pulmonary emboli, intertriginous dermatitis, urinary stress incontinence, gastro esophageal reflux disease (GERD), gall stones, and sclerosis and carcinoma of the liver. In women, infertility, cancer of the uterus and cancer of the breast are also associated with morbid obesity. Taken together, the diseases associated with morbid obesity markedly reduce the odds of attaining an average lifespan and raise annual mortality in affected people by a factor of 10 or more.

Current treatments for obesity include diet, exercise, behavioral treatments, medications, surgery (open and laproscopic) and endoscopic devices. There are currently three (3) weight loss drugs approved by the U.S. Food and Drug Administration. Orlistat (XENICAL®) provided by Roche is a non-systemic inhibitor of the enzyme lipase that works by interrupting the action of lipase in breaking down fats. Sibutramine hydrochloride (MERIDA®) is a non-amphetamine appetite suppressant that inhibits brain chemicals involved in appetite, thereby promoting a signal of satiety. Phentermine (ADIPEX-P®) is a structural analog of amphetamine and is also an appetite suppressant indicated for exogenous obesity.

In addition, there are currently a number of clinical trials on-going for treatments of obesity. One line of enquiry is based around the chemistry of the hormone called Human Amylin, which plays a role in the regulation of appetite and food intake. Mid-stage clinical trial results with one of these products have shown a weight loss of 3.5 kg (7.7 lbs) over 60 weeks. While these drugs have shown signs of greater efficacy, there has not been developed any high efficacy pharmaceutical treatment. Further, the issue of short-term and long-term side effects is always of concern to consumers, pharmaceutical providers and their insurers.

Laporoscopic bariatric surgical procedures in current use include Laporoscopic V or vertical gastroplasty, laporoscopic gastric bypass with Roux Y Limb and a Laporoscopic Placement of Lap Band. These procedures have been reported to result in marked lasting weight reduction in the majority of morbidly obese patients when assessed five years after operation. Studies of the health-related quality of life outcomes of these procedures have documented sustained significant improvements in all parameters measured. Diet or drug therapy programs have been consistency disappointing and fail to bring about significant, sustained weight loss in the majority of morbidly obese people.

Currently, most (95%) morbid obesity operations are, or include, gastric restrictive procedures, involving the creation of a small (15-35 ml) upper gastric pouch that drains through a small outlet (0.75-1.2 cm), setting in motion the body's satiety mechanism. About 15% of morbid obesity operations done in the United States involve gastric restrictive surgery combined with a malabsorptive procedure. This divides small intestinal flow into a biliary-pancreatic conduit and a food conduit. Potential long-term problems with surgical procedures are notorious and include not only those seen after any abdominal procedure, such as ventral hernia and small bowel obstruction, but also those specific to bariatric procedures such as gastric outlet obstruction, marginal ulceration, protein malnutrition and vitamin deficiency.

Additionally, there are in development multiple endoscopic procedures for obesity. Endoscopically placed gastric balloons restrict the gastric volume and result in satiety with smaller meals. Endoscopic procedures and devices to produce gastric pouch and gastrojejunal anastomosis to replicate laporoscopic procedures are also in development. These procedures, however, are not without their risks.

Gastric electric stimulation (GES) is another procedure that is currently in clinical trial. Gastric Electrical Stimulation (GES) employs an implantable, pacemaker-like device to deliver low-level electrical stimulation to the stomach.

The procedure involves the surgeon suturing electrical leads to the outer lining of the stomach wall. The leads are then connected to the device, which is implanted just under the skin in the abdomen. Using an external programmer that communicates with the device, the surgeon establishes the level of electrical stimulation appropriate for the patient.

While the exact way in which GES causes weight loss is not fully understood, it is believed that through low-level electrical pulses the therapy slows the intrinsic electrical waves in the stomach. Animal studies have shown that this electrical stimulation causes the stomach to relax, resulting in distension of the stomach. This distension triggers nerves in the stomach involved in digestion to send signals via the central nervous system to the brain that the stomach is "full".

GES may also result in a decrease in gastrointestinal hormones such as CCK, somatostatin GLP-1 and leptin, all of which are associated with hunger. Recent work on GES has shown promising results in obese patients. GES results in 35% EWL (excess weight loss) beyond 24 months and the results are sustained and replicated. This technology is currently available in Europe and Canada and undergoing trials for FDA approval in the U.S U.S. Pat. No. 6,901,295 to the present applicant describes a method and apparatus for electrical stimulation of the lower esophageal sphincter (LES). The device and method are directed toward inducing contraction of the LES to thereby combat gastro esophageal reflux disease (GERD). The claimed invention is directed towards using, amongst other things, sensing electrodes in the esophagus for detecting esophageal peristalsis so as to inhibit the electrical stimulation of the lower esophageal sphincter in order to pass food to the stomach. The disclosed device and method, therefore, increases LES tone after passage of food to the stomach. It is designed to prevent gastric reflux of acid material.

Published US Patent Application No 2005/0065571 to Imran discloses a responsive gastric stimulator which senses one or more parameters and then affects smooth muscle contractions and nerves associated with the stomach and/or biochemistry or secretions of the stomach. Stimulation may be directed to cause gastric retention of food for a greater duration by interfering with peristaltic contractions and/or the innate electrical potentials of the stomach.

Published US Patent Application No 2005/0090873 to Imran discloses a fixation device for holding stimulating electrodes in electrical contact with the wall of a portion of the gastrointestinal tract. This device comprises an expandable member that fixes electrodes in electrical contact with the gastrointestinal tract. The disclosure also extends to a method for treating obesity by controlling the pylorus to retain food in the stomach for a desired period of time to provide a sensation of satiety and/or to reduce hunger. The disclosed invention is relatively cumbersome and involves the intra-luminal insertion of an expandable member that presents some degree of risk in the duodenum. Food must be able to pass through the device while at the same time its expansive pressure must be sufficient to hold electrodes in place, but not damage the wall of the small intestine. The method and device also seek to control contraction of the pylorus by electrical stimulation of the duodenum.

Published US Patent Application No 2003/0144708 to Starkebaum relates to a method and system for treating patients with eating disorders, including obesity, through the delivery of electrical stimulation directly or indirectly to the pylorus of a patient to close the pyloric lumen to inhibit emptying of the stomach.

Published US Patent Application No 2004/0015201 to Greenstein discloses a process for electro-stimulation treatment of obesity. This disclosure is directed to electro-stimulation of the stomach, the lower esophageal sphincter, the pyloric sphincter and the ileo-caecal sphincter.

International Publication No WO2005/051486 to University Technologies International Inc. discloses a method and apparatus for gastrointestinal motility control. This discloses a complex multi-channel implantable device using one or multiple micro-system controlled channels and circumferentially arranged sets of two more electrodes to provide externally-invoked synchronized electrical signals to the smooth muscles via the neural pathways. The applicant describes invoking peristalsis but also corrupting peristalsis by implanting electrodes in the pyloric region or other areas of the stomach. The claimed invention relates to electrically-stimulating patches in the vicinity of an organ until the organ relaxes and applying electrical energy to the gastrointestinal tract to invoke a desired motility result. The identified specification does not disclose any means of feedback.

U.S. Pat. No. 6,611,715 to Boveja describes an apparatus and method for treating obesity and compulsive eating disorders using an implantable lever receiver and an external stimulator. The lead-receiver is in electrical contact with the left vagus nerve. The device is used for neuromodulating the vagus nerve with a result of appetite suppression.

SUMMARY OF THE INVENTION

It is an object of the present invention to provide a method and apparatus for increasing UES, esophageal or LES sphincter tone to decrease or delay esophageal emptying. The present invention may also extend to delaying emptying of the stomach and increasing satiety in a subject.

It is an object of the present invention to provide a method and apparatus for increasing UES, esophagus or LES tone to decrease or delay esophageal emptying.

It is also an object of the present invention to provide a method and apparatus for preventing or limiting esophageal emptying by increasing UES, esophageal or LES tone without causing permanent injury to the surrounding tissue or organs.

It is a further object of the present invention to provide a method and apparatus for preventing or restricting esophageal emptying by increasing UES, esophageal or lower esophageal or LES tone that is variable by changing the duration, power and frequency of stimuli without requiring subsequent endoscopic surgical or radiological procedures.

It is a still further object of the present invention to provide a method and apparatus for treating obesity by providing electrical stimulation to the UES, esophagus or LES or nerves supplying the structures through the use of one or more electrodes. The method and apparatus may be supplemented by further including stimulation of the stomach, and/or pylorus.

It is another object of the present invention to provide a method and apparatus for the stimulation of the gastric fundus to interfere with receptive relaxation and/or gastric accommodation to induce satiety.

It is a further object of the present invention to monitor physiological parameters and to modulate electrical stimulation according to changes in those parameters.

It is also an object of the present invention to provide a method and apparatus of preventing or limiting pyloric relaxation only in response to a nutrient rich meal.

It is a further object of the present invention to apply any of the above methods in combination with stimulation of the vagal nerve, small intestine, or colon.

In a first broad aspect, the invention resides in a method of modifying activity of the gastrointestinal tract in a subject.

A method of modifying activity of the gastrointestinal tract in a subject including the steps of electrically stimulating one or both of the upper esophageal sphincter and the esophagus to induce contraction of smooth muscle therein. The method may further comprise the step of electrically stimulating one or more of the LES, the stomach and the pyloric sphincter as well as, optionally, stimulating the vagus nerve, small intestine or colon.

In a further aspect, the invention may reside in a method of electrically stimulating one or more structures in the gastrointestinal tract to increase muscle tone by arranging a plurality of stimulating electrodes within or adjacent a portion of the gastrointestinal tract so that electrical stimuli causes the one of more structures to contract and wherein the structure is the UES and/or the esophagus. The method may further incorporate the step of placing a plurality of stimulating electrodes in communication with LES, the stomach and/ or the pyloric sphincter; small intestine or the colon wherein electrical stimuli from the stimulating electrodes causes the respective structure to contract. The method may include the step of stimulating the vagus.

In yet a further aspect, the invention may reside in a method of electrically stimulating one or more structures in the gastrointestinal tract by:

arranging a plurality of stimulating electrodes within a portion of the gastrointestinal tract;

providing electrical energy to the stimulating electrodes to thereby cause the structure to be stimulated;

arranging one or more sensing electrodes to detect change in physiological parameters in the blood or the gastrointestinal tract and modulating the stimulating electrodes in response to the change detected in the blood or the gastrointestinal tract to modify operation of the one or more structures.

The method may preferably relate to the UES, the esophagus, the LES and/or the vagus. The one or more structures may further include the stomach and/or the pyloric sphincter, small intestine or the colon.

The one or more physiological parameters may include esophageal peristalsis, esophageal pH, esophageal impedence, esophageal electrical activity, gastric peristalsis, gastric electrical activity, gastric chemical activity, intra-gastric temperature, pH or impedence; blood chemical and hormonal activity; vagal electrical or chemical activity.

One or more sensing electrodes may be positioned in one or more of the esophagus, the stomach the small intestine, colon, vagus or patients vascular system.

In yet a further aspect, the invention may reside in a device for electrical stimulation of a structure in the gastrointestinal tract wherein the device includes:

a pulse generator;

a plurality of stimulating electrode sets connected through wires or wirelessly to the pulse generator and adapted to be positioned within or adjacent the structure or in contact with nerves innovating the structure; and one or more sensing electrodes for monitoring physiological parameters; and means for varying activity of the stimulating electrodes in response to change detected in the physiological parameters to thereby modify operation of the structure.

The means for varying activity may be a microprocessor device and preferably also includes a power source. The structure may be one or more of the UES, the esophagus, the LES, the stomach, the pyloric sphincter the vagus, the small intestine and the colon. The shape of the electrical stimulation may be any suitable shape, preferably sinusoidal, square, rectangular or saw-toothed. The frequency of stimulation is preferably in the range of 1 Hz-1 MHz. The pulse generator may be connected to the electrode sets by wires or wirelessly. The sensing electrodes may be connected to the microprocessor by wires or wirelessly. The device may also be turned on or off by the patient at appropriate time related to the meal.

The above method and device may be applied for the treatment of obesity.

It is a further object of the present invention to provide a method and apparatus for preventing or slowing esophageal emptying by increasing UES, esophageal or LES sphincter tone without causing permanent damage to the surrounding tissue or organs as well as optionally delaying gastric emptying and increasing sense of satiety. The present invention may also be used to treat GERD by stimulating the LES and/or the esophagus to prevent gastric reflux after eating.

BRIEF DESCRIPTION OF THE DRAWINGS

To enable the invention to be fully understood, reference will now be made to the accompanying illustrations, in which.

DESCRIPTION OF THE PREFERRED EMBODIMENT

Figure 1:
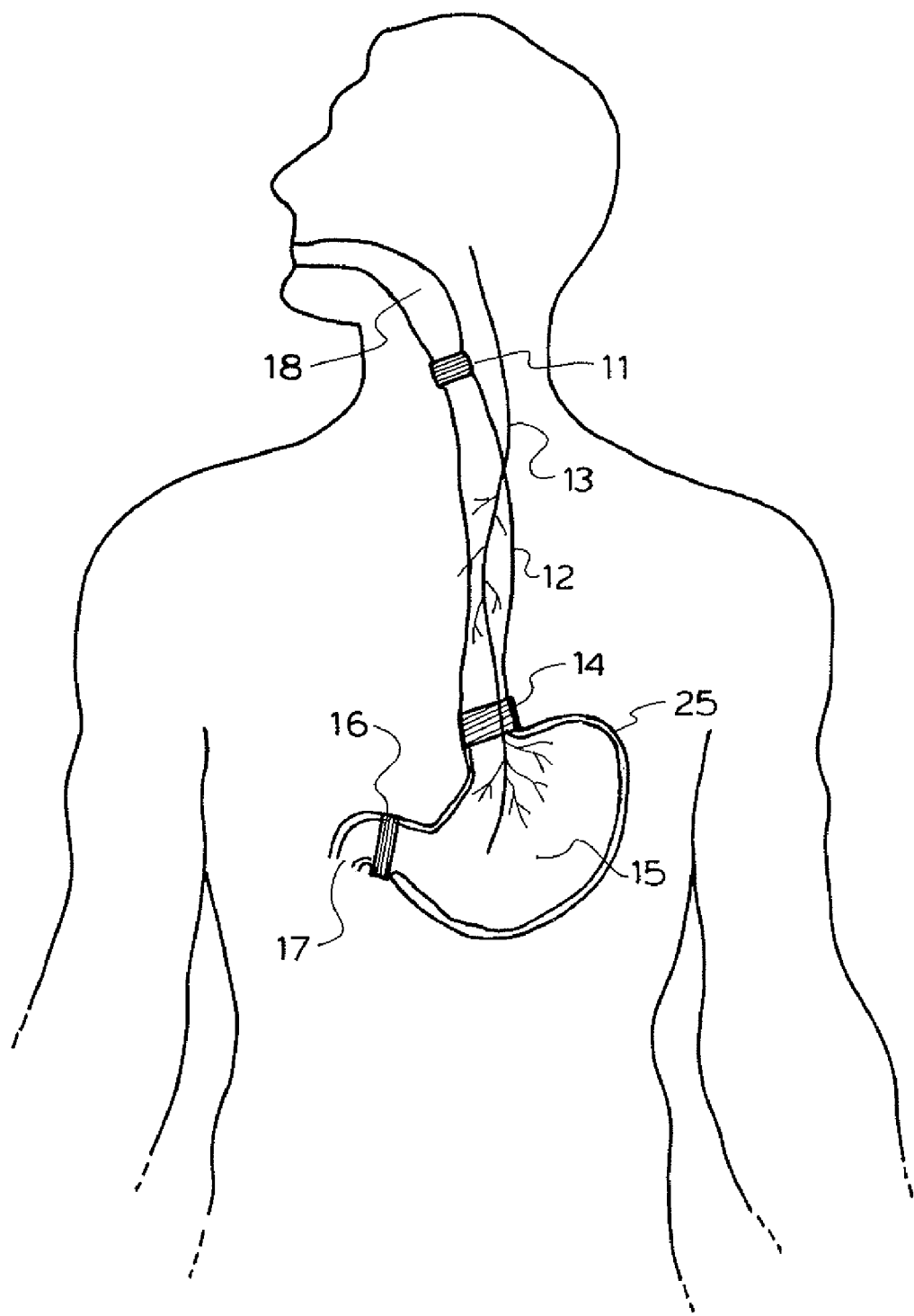
FIG. 1 is a schematic illustration of a portion of the gastrointestinal tract.

Referring to FIG. 1, there is seen a portion of the gastrointestinal (GI) tract, including the upper esophageal sphincter (UES) 11, esophagus 12, lower esophageal sphincter 14, stomach 15, pyloric sphincter 16 and duodenum 17. The UES 11 connects the oropharynx 18 and esophagus 12 and acts as a barrier to impede the passage of oral contents into the esophagus. The UES is contracted and therefore closed in a fasting state and undergoes periods of relaxation during the feeding or swallowing phase so as to allow oral contents to pass into the esophagus.

The LES 14 connects the esophagus 12 to the stomach 15 and acts as a barrier to impede the passage of esophageal contents into the stomach. The LES also acts to prevent regurgitation of stomach acid contents into the lower esophagus. The LES is contracted in a fasting state and undergoes periods of relaxation during the feeding or swallowing phase so as to allow the esophageal contents to pass into the stomach. The LES is a smooth muscle.

LES spasm or non-relaxation results in delayed esophageal emptying which, in turn, results in difficulty swallowing, early satiety and a resultant weight loss.

The pyloric sphincter 16 is located between the stomach and the duodenum and acts as a barrier to impede the passage of gastric contents from the stomach to the duodenum. The pyloric sphincter is in a contracted phase in the fasting state and undergoes periods of relaxation during the post-feeding phase to allow gastric contents to flow from the stomach into the duodenum 17.

The vagus or vagal nerve 13 is the dominant parasympathetic innervation to the upper G.I. and modulates perception and G.I. motor functions. Afferent vagal fibres from the stomach wall increase their firing rate when the stomach is filled with nutrients. Accordingly, extra physiological electrical stimulation of the vagus nerve from just above the stomach level may produce appetite suppression, by causing a patient to experience satiety. The left vagus nerve is preferred for siting the present invention as it provides minimal innervation to the cardiopulmonary system and mainly innervates the visceral organs such as the gastrointestinal tract. Stimulation of the left vagus nerve therefore can be expected not to cause any deleterious cardio pulmonary side effects. The fundus 25 of the stomach normally relaxes in response to a meal, thus allowing for accommodation of food bulk.

Figure 2:
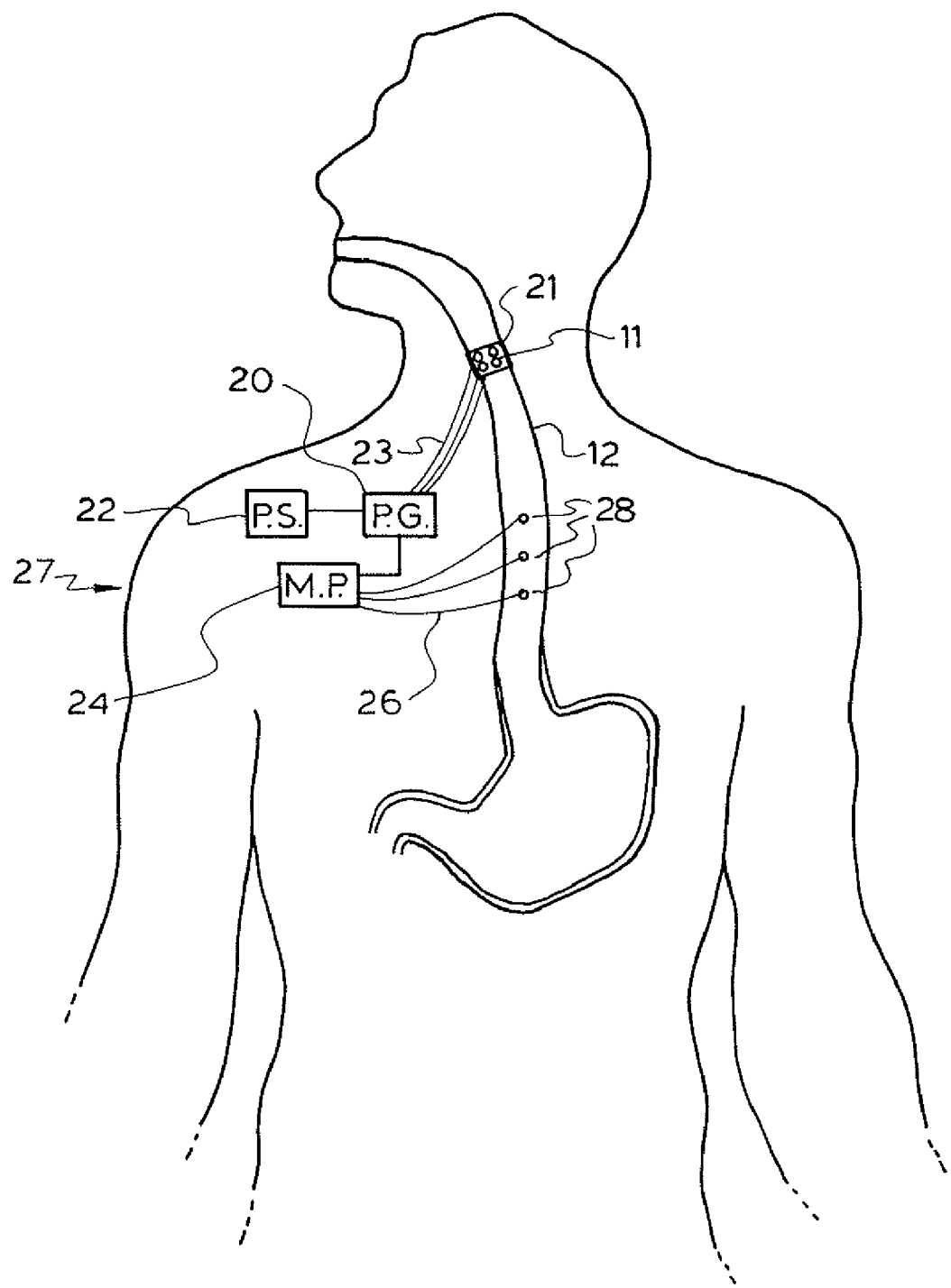
FIG. 2 is a schematic representation of the device of the present invention with stimulating electrodes implanted in the upper esophageal sphincter.

Referring to FIG. 2, there is seen a first embodiment of the present invention wherein a plurality of electrode sets 21 is placed in a loose linear configuration in the upper esophageal sphincter (UES). A pulse generator 20 is provided for stimulation of the electrodes and corresponding portion of the G.I. tract. The pulse generator 20 is connected to a power source 22 for supplying a source of power. The pulse generator 20 is further connected to the electrode sets 21 by wires 23 for applying the electrical stimulus to the electrode sets 21.

Alternatively, the electrode sets 21 may be coupled to the pulse generator 20 in a wireless fashion using an RF link, an ultrasonic link, a thermal link, a magnetic link, an electromagnetic link or an optical link. The power source 22 can be either a direct current source or an alternating current source. The number of electrode sets is determined by a number of factors, including the size of the electrodes, their power and the size of the desired placement area. Preferably, the pulse generator 20 is controlled by a microprocessor 24 for applying the electrical stimulus for periods of variable duration and variable power/frequency, so as to produce the preferred contraction or contractions.

Sensing electrodes 28 may be located in the esophagus 12 and electrically connected by wires 26 to the microprocessor 24. Alternatively, the sensing electrodes 24 may be in wireless communication with the microprocessor. The sensing electrodes may be selected to sense one or more physiological parameters in the esophagus. The physical parameters may include esophageal peristalsis, pH, pressure, temperature and impedance. Upon sensing appropriate changes in esophageal peristalsis, pH, pressure, temperature and/or impedance, the electrical stimulation in the upper esophageal sphincter may be initiated so as to contract the upper esophageal sphincter and impede passage of food from the oropharynx into the esophagus, thereby increasing the time of mastication, reducing the food intake and, preferably, increasing stimulation of the satiety centre. Stimulation of the UES may occur in the absence of the sensing electrodes 28 and the device may comprise the pulse generator 20, power source 22, microprocessor 24, electrical sets 21 and the wires or optionally a wireless arrangement. Stimulation of the UES may be timed to coincide with eating and may even be controlled by an external control unit.

Figure 3:
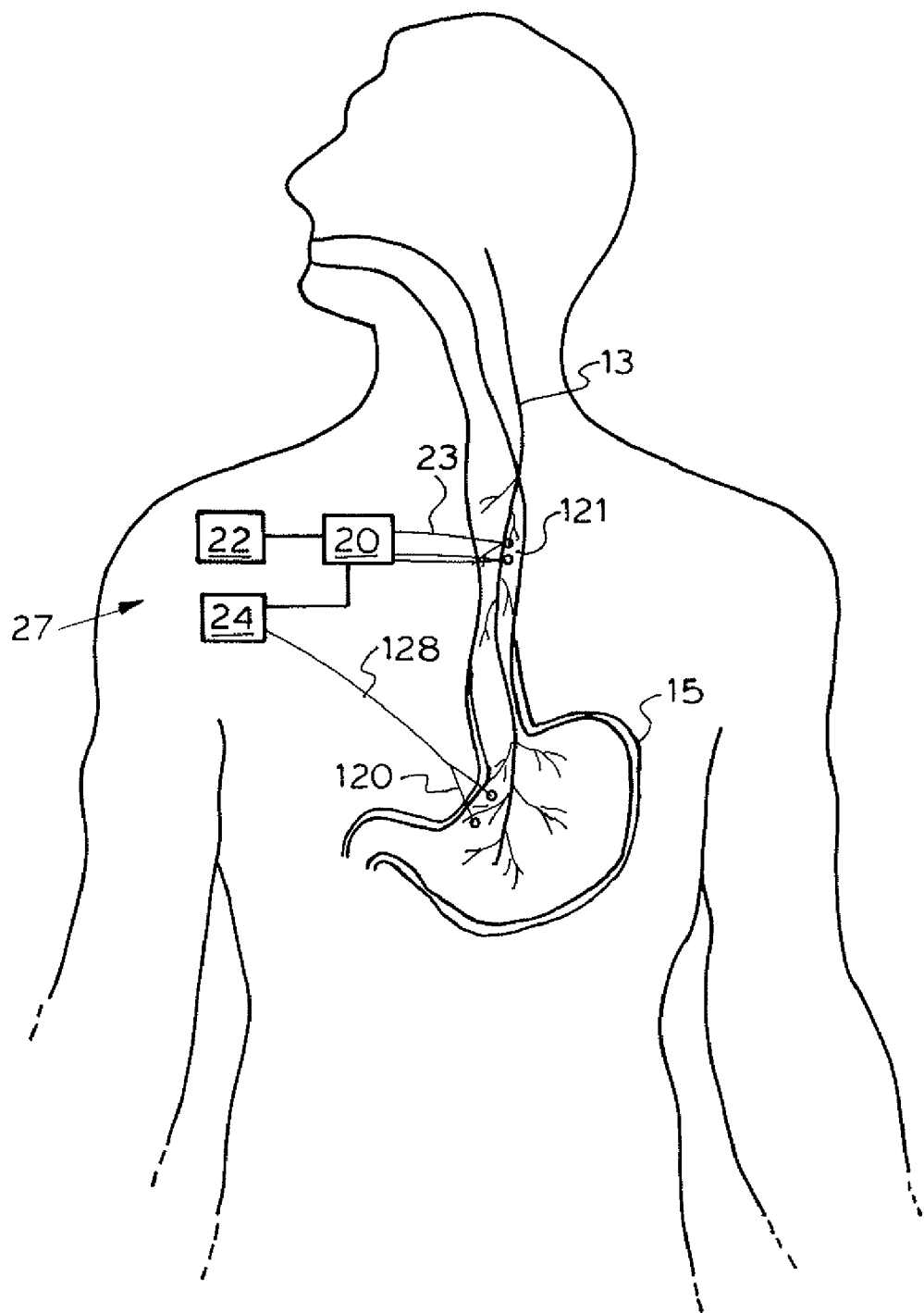
FIG. 3 is a schematic representation of a device of the present invention with stimulating electrodes implanted in association with the vagus.

Referring to FIG. 3, there is seen a device 27 comprising a pulse generator 20, power source 22 and microprocessor 24 as previously described. The device 27 is in electrical connection, either by wire or wirelessly, with stimulating electrode sets 121 located on or in communication with the vagus 13. Sensing electrodes 120 are in communication with the microprocessor 24 by a wire 128 although, optionally, the connection may be wireless. The sensing electrodes in this circumstance are positioned in the stomach and may be adapted to sense the status of one or more physiological parameters. The physiological parameters may include but are not limited to stomach acidity, peristalsis, impedence, pressure, temperature, tone and electrical activity. Changes in the physiological parameters may be detected by the microprocessor 24 with subsequent stimulation or cessation of stimulation of the vagus 13 through stimulating electrodes 121. For example, a sensation of increased peristalsis and muscle tone or pH change may indicate the presence of food in the stomach 15, therefore leading to stimulation of the vagus 13 with consequent sensation of satiety in the subject.

Figure 4:
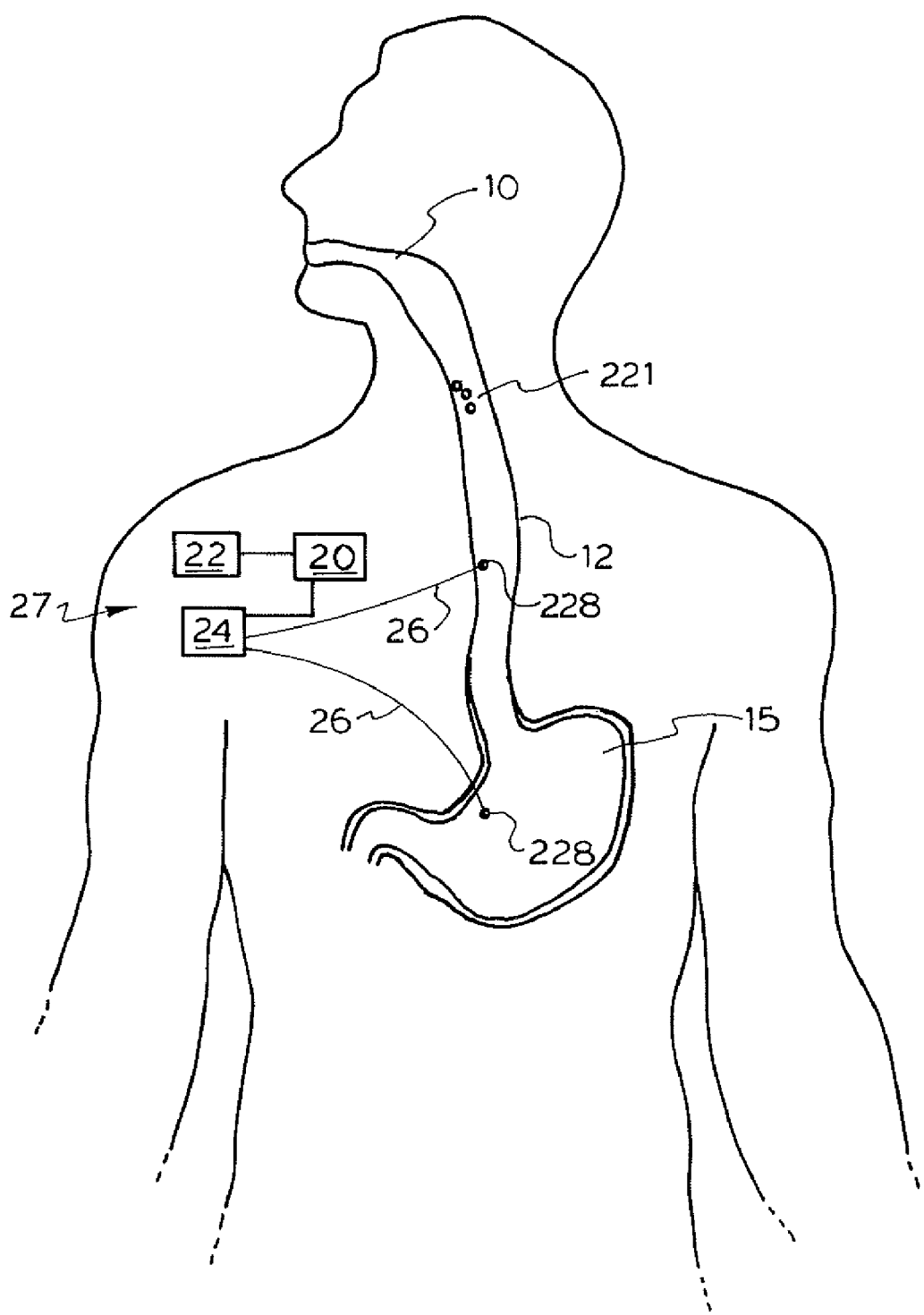
FIG. 4 is a schematic representation of a device of the present invention with stimulating electrodes implanted in the esophagus.

FIG. 4 shows a device 27 as previously described comprising a pulse generator 20, power source 22 and microprocessor 24. A plurality of electrode sets 221 are placed in the esophagus 12, preferably in a loose linear configuration. Although shown as located in the proximal portion of the esophagus 12, the electrode sets may be positioned as preferred for ease of access, placement and operation. The electrodes 221 and the pulse generator are in wireless communication. Sensing electrodes 228 are shown in this case with one in the esophagus and one in the stomach. The sensing electrodes are adapted to determine physiological parameters, such as are described above. The sensing electrodes 228 are in communication with the microprocessor 24 by wires 26 but may optionally be in wireless communication.

In one embodiment, the device 27 does not include sensing electrodes and is simply a stimulating arrangement for stimulating the smooth muscle of the esophagus 12 to contract as required. Contraction may be initiated during feeding times by the patient to limit the passage of food from the oropharynx 10 to the stomach 15, thereby stimulating the satiety centre or inducing a sensation of longer feeding in the patient. The sensing electrodes may be sited as preferred and may be in the esophagus, in the stomach or at another appropriate anatomical region.

Figure 5:
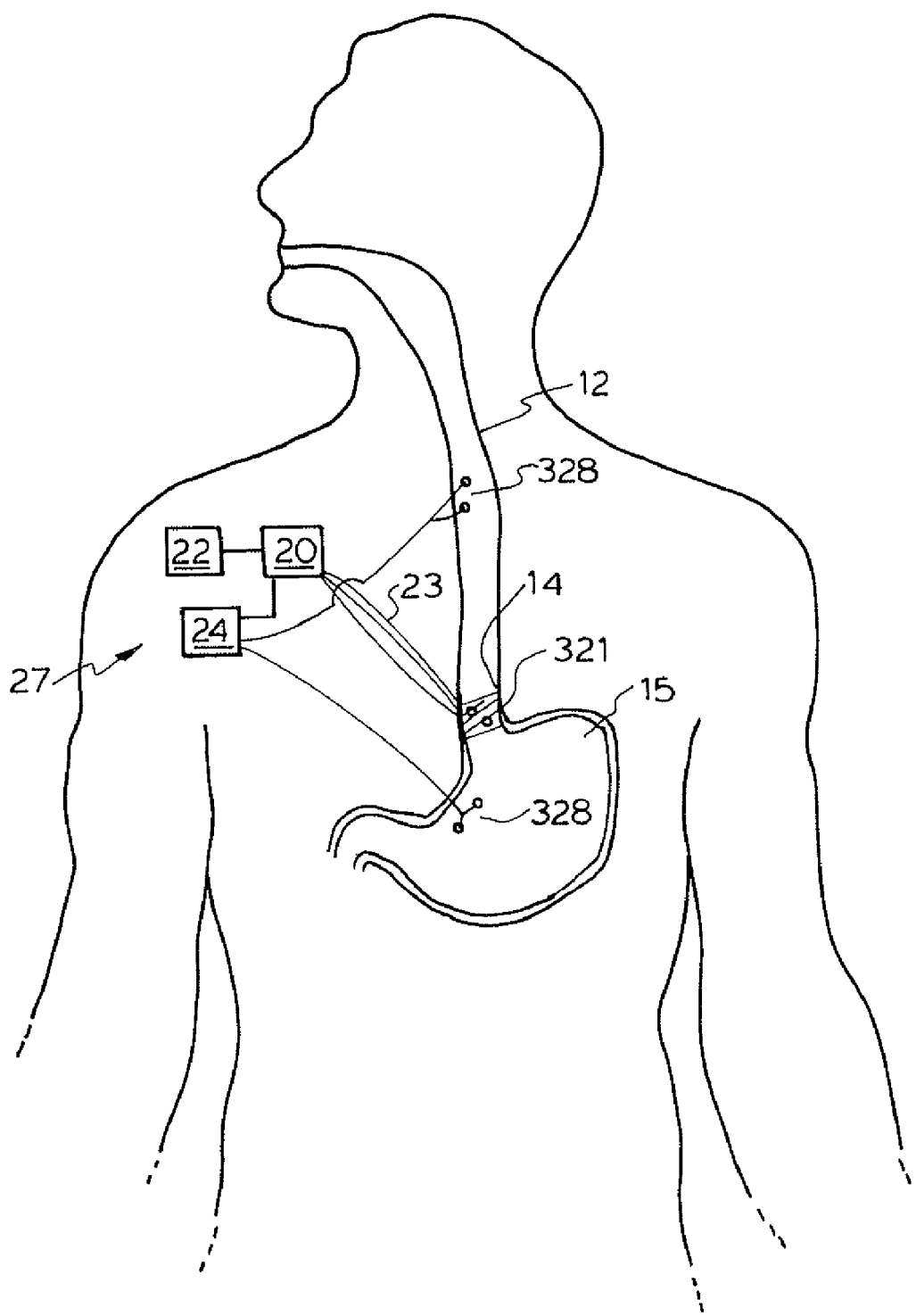
FIG. 5 is a schematic representation of the present invention with stimulating electrodes implanted in the lower esophageal sphincter.

In FIG. 5 there is shown an embodiment of the present invention wherein the device includes stimulating electrodes 321 placed in a loose linear pattern in or near the LES 14 and in communication with a pulse generator 20 connected via wires 23 or, optionally, in wireless communication with the pulse generator 20. Stimulation of the electrodes 321 causes contraction of the LES and, thereby, restricts entry of food from the esophagus 12 into the stomach 15. It is preferred that contraction of the LES occurs during feeding. However, the present invention may also be used to treat GERD, during non-feeding times by inducing stimulation of the LES during non-feeding periods. The present device therefore has considerable utility and versatility. This limits entry of food into the stomach and thereby decreases overall caloric intake.

The device 27 preferably includes sensing electrodes 328 for determining the status of preferred physiological parameters and, either detecting changes in the status or providing information to the microprocessor 24 to determine changes. The function of all sensing electrodes may be similar to this description. Changes indicative of feeding may induce stimulation of the stimulating electrodes 321 and cause contraction of the LES. Of course, it is possible to have the sensing electrodes in the same region as the stimulating electrodes if preferred. In one embodiment, the electrodes may include both a stimulating and sensing function.

In addition, the stimulating electrodes 321 can be programmed to stimulate the LES in response to changes in physiological parameters associated with acid or non-acid reflux sensed by the sensing electrodes 328 in order to treat obesity associated gastro-esophageal reflux disease.

Figure 6:
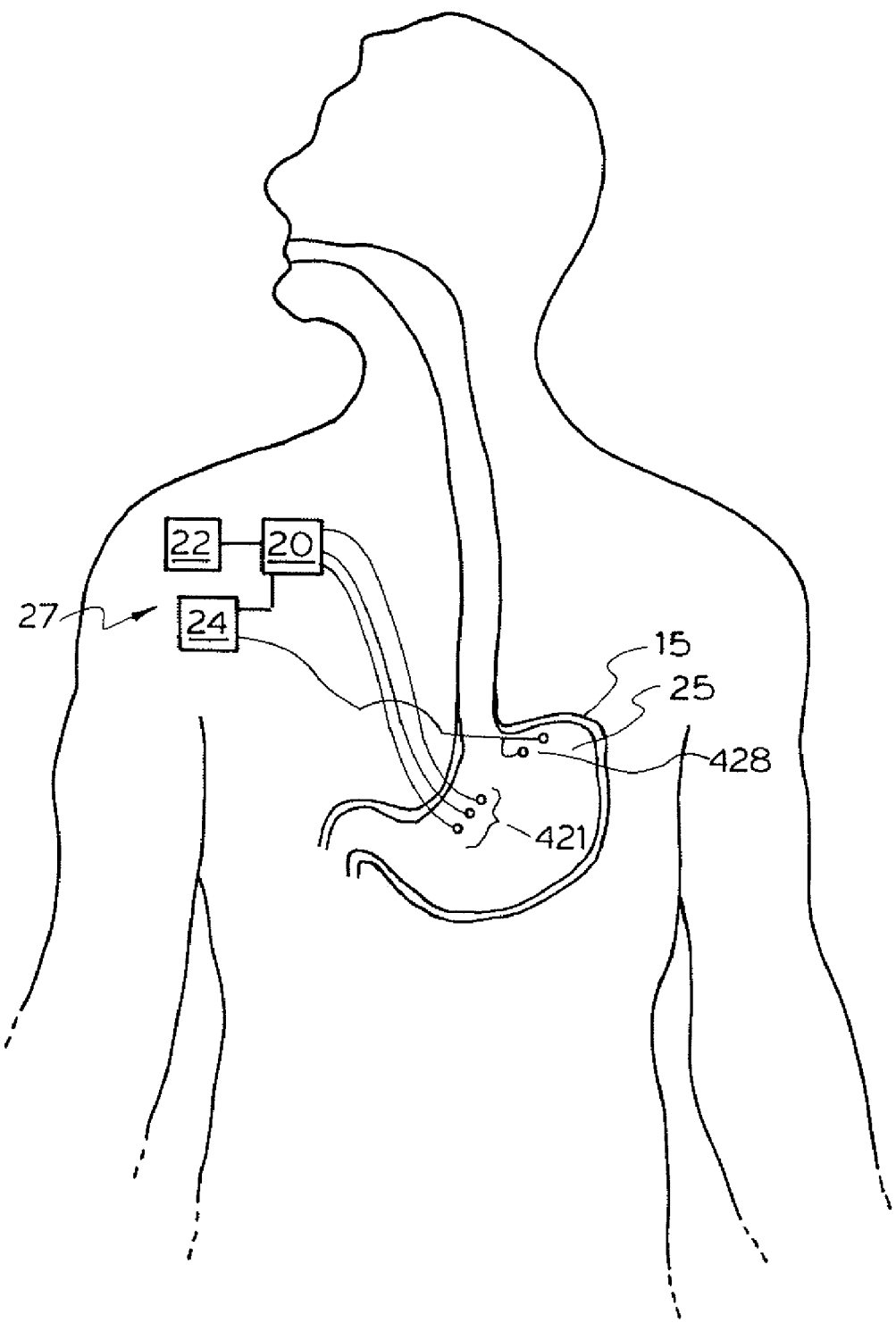
FIG. 6 is a schematic representation of the present invention with stimulating electrodes implanted in the stomach.

FIG. 6 shows a device 27 with a plurality of stimulating electrode sets 421 positioned in the stomach 15. The device includes a pulse generator 20, power source 22 and microprocessor 24 in communication with each other. Sensing electrodes 428 are positioned in the stomach 15 and in communication with the microprocessor 24. The sensing electrodes are formed as a plurality of electrode sets which are designed to detect one or more preferred physiological parameters. Changes in the parameters may be determined by the sensing electrodes and/or the microprocessor 24 of the resultant stimulation as appropriate of the fundus 25 via the plurality of electrode sets 421. For example, the stimulation of the sensing electrodes 428 by a drop in pH indicating secretion of stomach acid, or by increased peristalsis or by increased impedence may lead to activation of the plurality of electrode sets 421 to cause contraction of the fundus 25 or disruption of normal receptive relaxation or accommodation of the stomach, thereby inducing a decrease in food intake and increased stimulation of the satiety centre.

Figure 7:
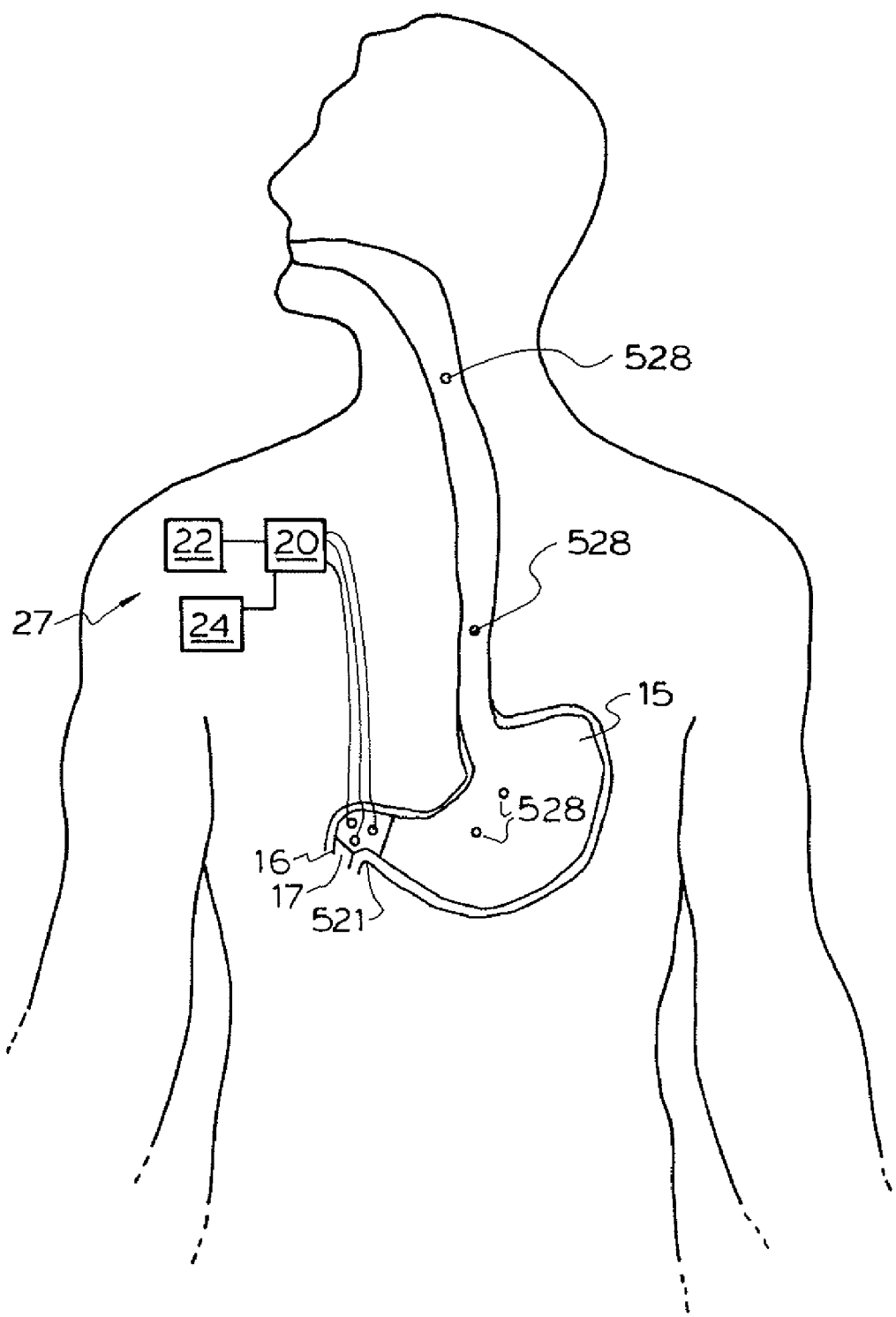
FIG. 7 is a schematic representation of the present invention with stimulating electrodes implanted in the pylorus.

In FIG. 7 a plurality of stimulating electrode sets 521 are implanted at or near the pylorus. Clearly, the electrode sets may be placed anywhere where the action is such as to cause contraction of the pylorus and may be proximal or distal thereto, provided the necessary activity is provided. This also applies to other structures in this specification, it is to be understood that stimulation of a structure includes stimulation of nerves innervating that structure and electrodes may be positioned accordingly. In this case, sensing electrodes 528 are positioned in the upper esophagus/lower esophagus/ stomach and are in wireless communication with the microprocessor 24. Stimulation of one or more of the sensing electrodes 528 may cause stimulation of the plurality of electrode sets 521 located in the pylorus. This precipitates contraction of the smooth muscle of the pyloric sphincter 16 with resultant restriction of movement of food into the duodenum 17, delayed emptying of the stomach 15 and decreased caloric intake of the subject.

The sensing and stimulating electrode sets may be placed in the mucosal, sub-mucosal, muscularis or serosal layer of the UES, esophagus, LES, stomach and pyloric sphincter and possibly duodenum. The electrode sets may be placed by endoscopic, surgical or radiological procedures. The stimulating electrodes may also be placed in operative relationship to the vagus or colon.

Each of the stimulating electrode sets preferably provides an electrical stimulus of less than 1 amp. The electrical stimulus can be provided continuously or intermittently. For example, one time or more per hour may be suitable in some circumstances. Over time, stimulation, whether continuous or intermittent, may serve to tone the smooth muscle of the UES, esophagus, LES, stomach or pylorus or other structure, with sufficient tone. Further electrical stimulation may be reduced or avoided. Depending on the patient, obesity may be successfully treated with a single treatment, or life-long stimulation may be required.

The electrical stimulus in the stimulating electrode sets may have any shape necessary to produce the desired result, including a square, rectangular, sinusoidal or saw-tooth shape. The frequency of the electrical stimulus is preferably in the range of approximately 1 Hz-1 MHz. The stimulus may be triggered by a transmitter (not shown) external to the body, similar to a remote transmitter for a cardiac pacemaker. With appropriate power settings and treatment periods, meal-induced UES, esophageal LES or pyloric relaxation is eliminated or minimised without causing permanent injury to the surrounding tissue or organs. The extent of this activity is preferably modified by monitoring indicative physiological characteristics. Objective measurement of the effects can be made by physical examination, serum chemical analysis or with a manometery catheter to measure UES, esophageal muscle, LES, stomach or pyloric muscle tone and function or by using barium radiography or scintigraphy to measure esophageal or gastric emptying. The sensing electrodes when included may be used to sense changes in esophageal or gastric pH, pressure, temperature, impedence due to feeding and thereafter appropriately modify (increase or decrease),
the electrical stimulus. The sensing electrodes can be included on or in the stimulating electrode sets to sense changes in physiological parameters such as esophageal or gastric pH, pressure, temperature, impedence, electrical activity or changes in blood chemistry, or hormone levels due to nutrients and appropriately modify increase or decrease of the electrical stimulus.

Additional sensing electrodes may be placed in the esophagus to monitor esophageal peristalsis, pH, pressure, temperature, electrical activity and/or impedence. Upon sensing an appropriate change, electrical stimulation of the pylorus may be initiated so that the pylorus can contract and impede passage of food from the stomach to the small intestine. Control of the pylorus can also be achieved by turning on or off the pulse generator. The stimulating electrode sets of this invention can be used in combination with additional pacing electrodes, as are known in the art, to treat disorders of acid reflux or gastric emptying or other gastrointestinal disorders.

In the preferred embodiments of the arrangement, there may be at least two spaced sites at which a respective plurality of stimulating electrodes are located.

Figure 8:
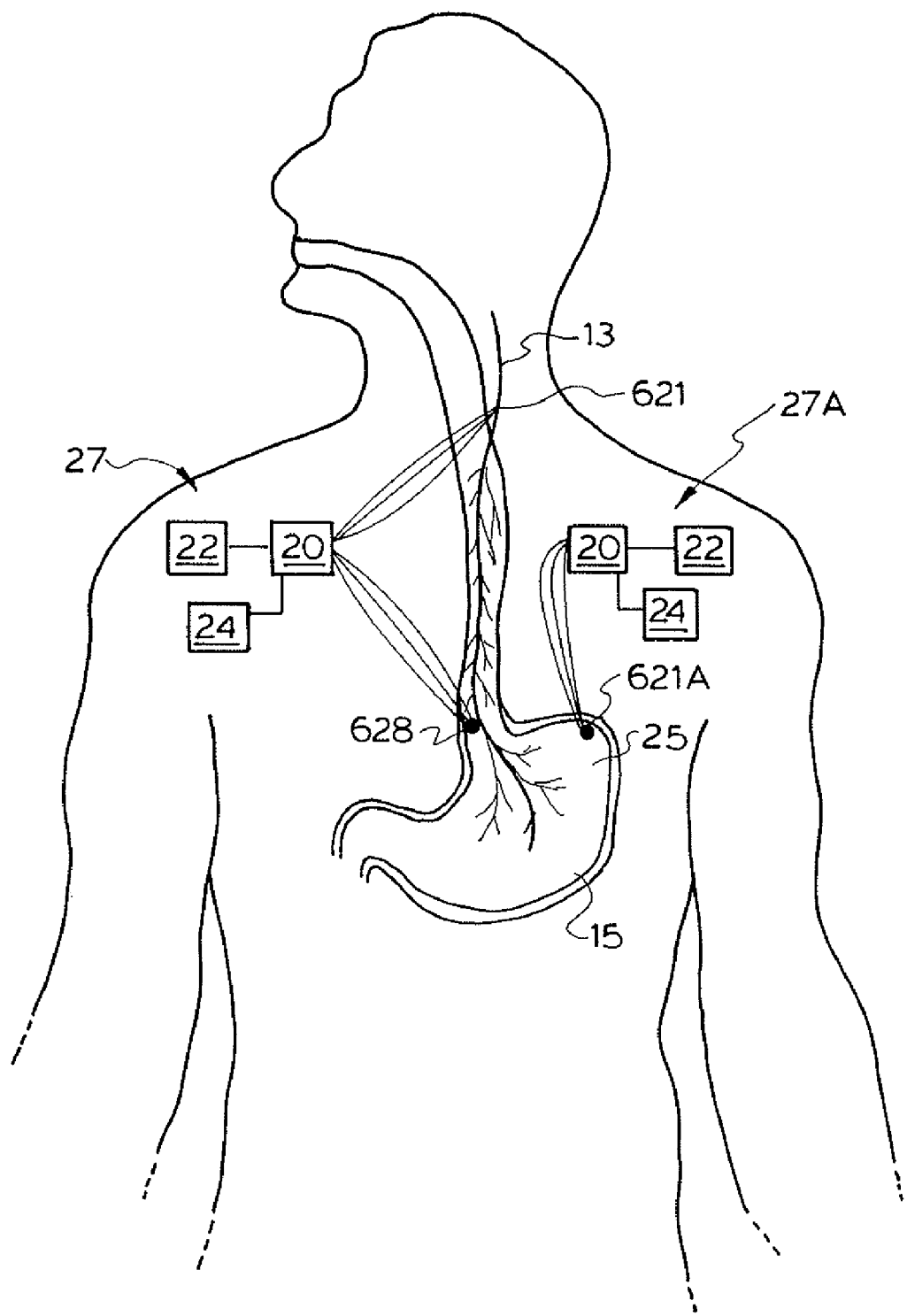
FIG. 8 is a schematic representation of the present invention with sensing electrodes in the stomach and stimulating electrodes in contact with the vagus and the stomach.

Referring to FIG. 8, there is seen a device 27 and a second device 27a, both comprising pulse generator 20, power source 22 and microprocessor 24 The two devices may be in communication with each other. One device may control more than one set of sensing and/or stimulating electrodes.

The first device 27 includes a plurality of stimulating electrodes 621 positioned on or in proximity to the vagus 13. Sensing electrodes 628 are positioned around the proximal stomach and LES. The electrode arrays may combine both sensing and stimulating functions. Sensing information is passed onto the microprocessor which is programmed to provide a suitable response to the pulse generator which in turn will stimulate or inhibit the stimulating electrode 621.

The second device 27A is in communication with a plurality of stimulating electrodes 621A positioned in a loose-linear configuration in the fundus 25 of the stomach 15 so that stimulation of the electrodes will cause contraction of the fundus of the stomach. The sensing electrodes 628 may also be in communication with the second device 27A and, in the present case, this would be via wireless communication. The advantage of the present invention becomes clearer in the present arrangement as the microprocessors may be programmed to provide a sophisticated response and a range of stimulation to the operative electrodes. Stimulation of the vagus 13 in tandem with delay of gastric accommodation/ receptive relaxation by stimulation of the electrodes 621A gives a double facet effect which, in some circumstances, may be accumulative or even synergistic. This may result in the need for less stimulation of the individual areas and less protracted stimulation before a permanent or extended benefit arises from the treatment. Although different devices 27, 27A are shown, it is clear that the capacity in the device may be such that different location electrodes, stimulating or sensing, may be controlled by one arrangement of the pulse generator, microprocessor and power source. The complexities of location and safety considerations will dictate the preferred arrangement. It is envisaged that the present invention may extend to any two or more combinations of stimulating electrode sets in two or more of the UES, the esophagus, the LES, the stomach, the pylorus, the small intestine, the colon and the vagus. Preferably, the effect of these arrangements are modulated by the presence of sensing electrodes which, again, may be in one or more multiple appropriate positions and adapted to sense the level or changes of physiological parameters such as temperature, pH, impedence, muscle tone and intestinal wall motility, or electrical activity.

Figure 9:
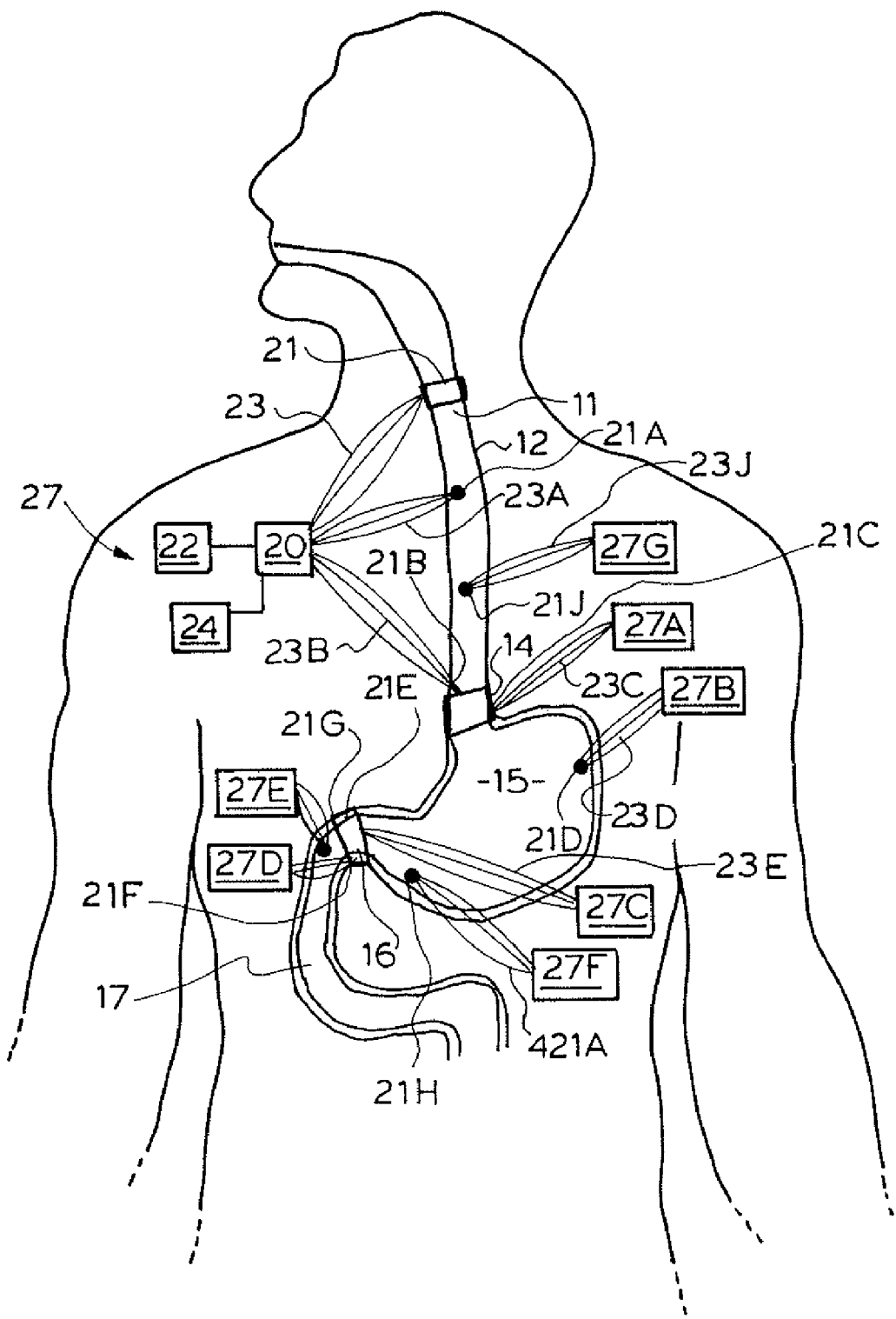
FIG. 9 is a schematic representation of one or more devices of the present invention with electrodes implanted in each of the upper esophageal sphincter, the esophagus, the lower esophageal sphincter, the stomach, the pylorus and the vagus.

Referring to FIG. 9, there is seen a complex arrangement which covers a number of the alternative configurations discussed above. While it is considered to be unlikely that any single patient would be subject to all these configurations, it is not impossible that it may be necessary if the patient is sufficiently compromised and the clinical condition requires such an input. A device 27 is shown in with a pulse generator 20, power source 22 and microprocessor 24. Wires 23 lead to a plurality of stimulating electrode sets 21 in the UES 11. Wires 23A also lead to a plurality of stimulating electrode sets 21A in the esophagus 12. A third set of wires 23B leads to a plurality of stimulating electrode sets 21B in the LES 14. All the stimulating sets may include sensing sets also in communication with the device via the microprocessor 24 and, in this case, by wireless communication although information on physiological parameters may be passed through the pulse generator to the microprocessor or through wired communication paths. A second device 27A which, in this case, is shown as a single encapsulated box also incorporates power supply, pulse generator and microprocessor as previously described which are not shown separately. Wires 23C connect to stimulating electrodes 21C. Sensing electrodes may be present and positioned around the stimulating electrodes 21C. A third device 27B is shown with wires 23D in communication with stimulating electrodes 21D in the stomach wall. A fourth device 27C is shown in communication with electrodes 21E which are stimulating electrodes through wires 23E and may include sensing electrodes proximal to the pylorus 16. A fifth device 27D is shown with electrodes 21F on or adjacent the pylorus 16, and a sixth device 27E is shown with electrodes 21G distal to the pylorus, but positioned to activate the pylorus. A seventh device 27F is shown with electrodes 21H positioned adjacent the lower greater curvature of the stomach 15. Wire connections are shown for each but they may be wireless.

An independent and eighth device 27G is shown with electrodes 21J on the esophagus 12 via wires 23J. A similar arrangement may be used in the small and/or large intestine.

A skilled addressee may choose the arrangement suitable for a patient. The arrangement may be independent devices or a single device with multiple foci of electrodes either stimulating alone or in combination with sensing electrodes. The device can also be remotely turned on and off by the patients or an appropriately designated person.

From the foregoing detailed description, it can be seen that the present invention provides an improved method and apparatus for electrical stimulation of one or more of the UES, esophagus, LES, stomach, pyloric sphincter, small intestine, colon and vagus.

Preferably, the stimulation is modulated in response to change detected in the blood, the gastrointestinal tract or the nerves supplying the gastrointestinal tract. The change may be in physiological parameters such as esophageal peristalsis, gastric peristalsis, gastric electrical activity, gastric chemical activity, intra-gastric temperature, muscle wall tone and pH. The present invention is preferably achieved by the placement of electrode sets in one or more of the UES, esophagus, LES, stomach, vagus or pyloric sphincter in an arrangement that induces contractions of the UES, esophagus, LES, stomach or pyloric sphincter, due to electrical stimulation of the surrounding tissue and nerves or induces a feeling of satiety by stimulation of the vagus. The electrical stimulation is preferably applied by a pulse generator for periods of variable duration and variable frequency, so as to produce the desired contraction.

It is notable that the UES, LES and pyloric sphincter are in a contracted phase in the fasting state and undergo periods of relaxation during the fed phase so as to allow food bolus to pass from the mouth into esophagus, stomach and the duodenum. In order to impede food from reaching the duodenum, an electrical stimulus is applied to one or more locations in the UES, esophagus, LES, stomach or the pyloric sphincter. These stimuli cause contraction of the UES, esophagus, LES, stomach and/or the pyloric sphincter and prevent or slow passage of a food bolus from the mouth to the duodenum. Alternatively or additionally, stimulation of the gastric fundus or vagus may increase the sensation of satiety and decrease caloric intake.

In particularly preferred embodiments, a plurality of electrode sets are placed in the G.I. tract near the UES, esophagus, LES, stomach, pyloric sphincter, small intestine, colon or the vagus and preferably near two or more. Each of the stimulating electrode sets may be comprised of at least one active electrode and at least one ground electrode. The electrode sets may be arranged in any pattern that produces the desired stimulation to the target region or structure and may include a circumferential pattern, a longitudinal axis, a regular pattern or other placement.

As used herein, the pyloric sphincter is a smooth muscle located between the stomach and the small intestine, that acts as a barrier to emptying of gastric contents into the small intestine. Pyloric relaxation allows for gastric contents to pass into the small intestine. Pyloric spasm or non-relaxation results in delayed gastric emptying which, in turn, results in early satiety and weight loss.

The LES is a muscle at the end of the esophagus that regulates emptying of esophageal content into the stomach. In addition, the LES also prevents reflux of gastric contents into the stomach. Esophageal emptying has been shown to be slowed and LES tone maintained by stimulating the LES to maintain it in the closed position, thus producing LES spasm.

The present invention, therefore, allows a clinician to selectively prevent UES, esophagus, LES, stomach or pylorus, relaxation during eating by stimulating one or more of the structures or nerves supplying the structures to thereby limit the intake of a patient.

The present invention may be used in a stimulating mode alone or in conjunction with sensing electrodes that sense physiological parameters and modulate the activation of stimulating electrodes. The physiological parameters may include esophageal peristalsis, esophageal pH or impedence, esophageal electrical activity gastric peristalsis, gastric pH, gastric temperature, gastric impedence, gastric electrical or chemical activity, antro-pyloric impedence, blood chemical activity or gastro-intestinal neural activity.

The advantages of the present invention include the ability to prevent pyloric relaxation only in response to, for example, a nutrient-rich meal which may be detected by changes in the physiological parameters. The present invention provides a relatively non-invasive and non-surgical response to eating disorders and clinical conditions such as obesity and related conditions.

Without being bound to any one theory, it appears direct stimulation of the gastric fundus may increase satiety by stimulating the gastric fundus and inhibiting gastric fundic receptive relaxation and accommodation. Gastric fundic receptive relaxation and accommodation occurs in response to meals and allows the stomach to accommodate the meals. Lack of gastric fundic receptive relaxation and accommodation results in symptoms of fullness and early satiety.

The present invention generally uses conventional laproscopic, endoscopic radiological, or other minimally invasive surgical techniques to place the desired device or devices on or adjacent to or in communication with the structure with which it is to be associated. Conventional electrode stimulation devices may be used in the practice of this invention. Such devices are well known to persons having ordinary skill in the art and may include those described in U.S. Pat. No. 5,423,872 which describes an implantable gastric electrical stimulator placed at the antrum area of the stomach which generates sequential electrical pulses; U.S. Pat. No. 5,690,691 for a portable or implantable gastric pacemaker employing a number of electrodes; U.S. Pat. No. 5,836,994 for an implantable gastric stimulator which incorporates direct sensing of the intrinsic gastric electrical activity; U.S. Pat. No. 5,861,044 for an implantable gastric stimulator sensing abnormal electrical activity of the gastrointestinal tract; PCT Application No. PCT/US98/10402 and U.S. patent application Ser. No. 09/424,324 for an implant device equipped with tines to help secure it in the appropriate location; U.S. Pat. No. 6,041,258 for an electrostimulation device with improved handle for laproscopic surgery; U.S. patent application Ser. No. 09/640,201 for an electrostimulation device attachable to enteric or endo-abdominal tissue or viscera which is resistant to attachment; PCT Application No PCT/US00/09910 entitled "Gastric Stimulator Apparatus and Method for Installing"; PCT Application No PCT/US00/10154 entitled "Gastric Stimulator Apparatus and Method for Use"; U.S. patent application Ser. No. 09/713,556 entitled "Improved Process for Electrostimulation Treatment of Morbid Obesity" These devices may be altered or varied as appropriate. All Patents, Patent Applications, Provisional Patent Applications and all Publications referred to in the specification are hereby incorporated by reference.

Although the present invention is especially adapted for treatment of obesity and/or control of weight, it may also be employed in treatment regimes involving other stomach-related disorders including, for example, relapsing peptic duodenal ulcer, gastric peptic disorders induced by duodenal gastric reflux, esophageal peptic disorders induced by gastric reflux and similar.

The method and devices used in the present invention are susceptible to numerous modifications and variations, all of which are in the scope of the present inventive concept. Furthermore, all the details may be replaced with technically-equivalent elements. Variations may be made according to practices and procedures of a skilled addressee.

The invention claimed is:

1. A method of electrically stimulating one or more structures in an upper esophageal sphincter or esophagus to modify activity of said upper esophageal sphincter or esophagus in order to treat gastrointestinal conditions of a patient, the method comprising the steps of: arranging at least two stimulating electrodes within a portion of said upper esophageal sphincter or esophagus, wherein said at least two stimulating electrodes are in different locations within said portion of said upper esophageal sphincter or esophagus; and triggering electrical stimuli from the stimulating electrodes when said patient enters a feed phase and wherein said stimuli causes said portion of said upper esophageal sphincter or esophagus to contract and wherein the electrodes are stimulated in a pattern that slows passage of a food bolus through the upper esophageal sphincter or esophagus.

2. The method of claim 1, further comprising the step of arranging a plurality of stimulating electrodes within or adjacent a lower esophageal sphincter wherein stimuli from the plurality of stimulating electrodes stimulate the lower esophageal sphincter.

3. A method of electrically stimulating an upper esophageal sphincter or esophagus of a patient, the method comprising the steps of: arranging at least two stimulating electrodes within different portions of said upper esophageal sphincter or esophagus; providing electrical energy to the stimulating electrodes to thereby cause at least one of said portion of the upper esophageal sphincter and an esophagus to be stimulated; arranging one or more sensing electrodes to detect change in one or more physiological parameters in a gastrointestinal tract; and modulating the stimulating electrodes in response to the change detected in the gastrointestinal tract, wherein said change is indicative of said patient entering into a feed phase, to modify operation of the portion of the upper esophageal sphincter or esophagus, wherein the electrodes are stimulated in a pattern that slows passage of a food bolus through the upper esophageal sphincter or esophagus.

4. The method of claim 3 wherein electrical stimuli from the stimulating electrodes are applied to nerves supplying the upper esophageal sphincter or esophagus.

5. The method of claim 3 wherein the one or more sensing electrodes detect change in the one or more physiological parameters selected from esophageal peristalsis, esophageal pH, esophageal impedance, esophageal pressure, esophageal electrical activity, gastric peristalsis, gastric electrical activity, gastric chemical activity, gastric hormonal activity, gastric temperature, gastric pressure, gastric impedence and gastric pH, blood chemical and/or hormonal activity, vagal or other gastrointestinal neural activity and salivary chemical activity.

6. The method of claim 3 wherein the one or more sensing electrodes are positioned in or adjacent one or more of the esophagus, the stomach, the small intestine, vagus or other nerves supplying the gastrointestinal tract and the vascular system.

7. The method of claim 3, further comprising a plurality of stimulating electrodes within or adjacent a lower esophageal sphincter wherein stimuli from the stimulating electrodes stimulate the lower esophageal sphincter.

8. A device for electrical stimulation of one or more structures in the gastrointestinal tract of a patient and for use in the treatment of gastrointestinal conditions, the device comprising: a pulse generator providing electrical stimulation; a power source for powering the pulse generator; a plurality of stimulating electrode sets connected to the pulse generator wherein the electrode sets are adapted to be positioned within different portions of at least one of an upper esophageal sphincter or an esophagus or in contact with nerves innervating the upper esophageal sphincter or the esophagus; and one or more sensing electrodes for monitoring physiological parameters; and a microprocessor programmed to vary activity of the stimulating electrodes in response to change detected in the gastrointestinal tract, wherein said change is indicative of said patient entering into a feed phase, to thereby modify operation of the upper esophageal sphincter or the esophagus, wherein the microprocessor is further programmed to stimulate the stimulating electrodes in a pattern that slows passage of a food bolus through the upper esophageal sphincter or esophagus.

9. The device of claim 8 wherein the electrical stimulation has a shape which is square, rectangular, sinusoidal or sawtooth and wherein the electrical stimulation has a frequency in the range of 1 Hz-1 MHz.

10. The device of claim 8 wherein the pulse generator is wirelessly connected to the electrode sets.

11. The device of claim 8 wherein the sensing electrodes sense one or more change in gastrointestinal, muscle tone, peristaltic activity, esophageal peristalsis, esophageal pH, esophageal pressure, esophageal impedance, esophageal electrical activity, gastric peristalsis, gastric electrical activity, gastric chemical activity, gastric hormonal activity, gastric temperature, gastric impedence, gastric pH, blood chemical and hormonal activity, vagal or other gastrointestinal neural activity and salivary chemical activity.

12. The device of claim 8 wherein the sensing electrodes are adapted to be positioned in or adjacent one or more of the esophagus, the stomach, the small intestine, the colon, the vagus or other gastrointestinal nerves and the vascular system.

13. The device of claim 8 wherein the gastrointestinal condition is obesity.

14. The device of claim 8, further comprising a plurality of stimulating electrode sets connected to the pulse generator wherein the electrode sets are adapted to be positioned within a lower esophagus esophageal sphincter or in contact with nerves innervating the lower esophageal sphincter.

* * * * *